US009863186B2

(12) United States Patent
Bimbo et al.

(10) Patent No.: US 9,863,186 B2
(45) Date of Patent: Jan. 9, 2018

(54) REVERSE TAPER MOUNTING OF SEPARATE COMPONENTS AND COUPLING OF DEVICES WITH REVERSE TAPER FITTINGS

(71) Applicant: SMITHS MEDICAL ASD, INC., Rockland, MA (US)

(72) Inventors: Frank A. Bimbo, Lawrenceville, GA (US); John Douglas Ilg, Peterborough, NH (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 639 days.

(21) Appl. No.: 13/940,410

(22) Filed: Jul. 12, 2013

(65) Prior Publication Data

US 2014/0027327 A1    Jan. 30, 2014

Related U.S. Application Data

(60) Provisional application No. 61/677,099, filed on Jul. 30, 2012.

(51) Int. Cl.
*A61M 3/00* (2006.01)
*E06B 9/52* (2006.01)
(Continued)

(52) U.S. Cl.
CPC ............... *E06B 9/52* (2013.01); *A61M 3/00* (2013.01); *A61M 5/3216* (2013.01); *E06B 9/01* (2013.01); *Y10T 29/4984* (2015.01)

(58) Field of Classification Search
CPC ... A61B 5/1405; A61B 1/1411; A61B 1/1433; A61M 5/3216
(Continued)

(56) References Cited

U.S. PATENT DOCUMENTS 1,950,947 A    3/1934  Mulroyan
1,907,059 A    8/1934  Schotter
(Continued)

FOREIGN PATENT DOCUMENTS

DE    2533594 A1    2/1976
JP    H07-502440 A    3/1995
(Continued)

OTHER PUBLICATIONS

Han, In Ho, ISA/KR, PCT International Search Report and Written Opinion (PCT/US2013/050182), dated Oct. 24, 2013.

*Primary Examiner* — J. Gregory Pickett
*Assistant Examiner* — James Way
(74) *Attorney, Agent, or Firm* — Louis Woo

(57) ABSTRACT

A medical device has a base having an internally tapered wall mounted to a neck of a tube holder that has a reverse taper, so that rotation of the base relative to the neck may be effected with a controlled drag to provide a smooth and secure relative rotation. The base may be rotated relative to the holder by rotationally moving a needle protection housing hingedly attached to the base. The housing may be rotated to any orientation relative to the tube holder so long as a torsional force greater than the predetermined friction between the tapered surfaces is applied thereto. The base is designed to have a ring at its base that biases against the base of the neck in a self-adjustable manner. Other devices may also be fitted with reverse tapered complementary connection fittings to securely couple to each other.

21 Claims, 6 Drawing Sheets

(51) Int. Cl.
    *E06B 9/01* (2006.01)
    *A61M 5/32* (2006.01)

(58) Field of Classification Search
    USPC .............. 206/210, 364, 367, 365; 604/192
    See application file for complete search history.

(56) References Cited

U.S. PATENT DOCUMENTS

| | | | |
|---|---|---|---|
| 4,012,885 A | | 3/1977 | King, Jr. |
| 5,154,285 A * | | 10/1992 | Hollister ................ 206/365 |
| 5,277,311 A | | 1/1994 | Hollister |
| 5,709,412 A | | 1/1998 | Vadas |
| 5,921,130 A | | 7/1999 | Yamada |
| 6,089,622 A | | 7/2000 | Vadas |
| 6,846,045 B2 | | 1/2005 | Sollami |
| 7,108,405 B2 | | 9/2006 | Matts et al. |
| 7,250,038 B2 * | | 7/2007 | Simpson et al. ........... 604/192 |
| 7,559,530 B2 | | 7/2009 | Korogi et al. |
| 7,594,911 B2 | | 9/2009 | Powers et al. |
| 7,635,071 B1 | | 12/2009 | Montgomery et al. |
| 7,637,904 B2 | | 12/2009 | Wingler et al. |
| 7,644,843 B1 | | 1/2010 | Bush et al. |
| 7,670,318 B2 * | | 3/2010 | Alesi et al. .................. 604/181 |
| 7,788,993 B2 | | 9/2010 | Wood |
| 7,883,502 B2 | | 2/2011 | Powers |
| 8,231,601 B2 | | 7/2012 | Reavill |
| 8,713,398 B2 | | 4/2014 | Kamiya |
| 2001/0004970 A1 * | | 6/2001 | Hollister et al. ............ 206/365 |
| 2007/0088261 A1 | | 4/2007 | Lew |
| 2011/0309615 A1 | | 12/2011 | Arstein et al. |

FOREIGN PATENT DOCUMENTS

| | | |
|---|---|---|
| JP | 09-057440 | 3/1997 |
| JP | 2009-287633 | 12/2009 |
| WO | 93/12991 | 7/1993 |

* cited by examiner

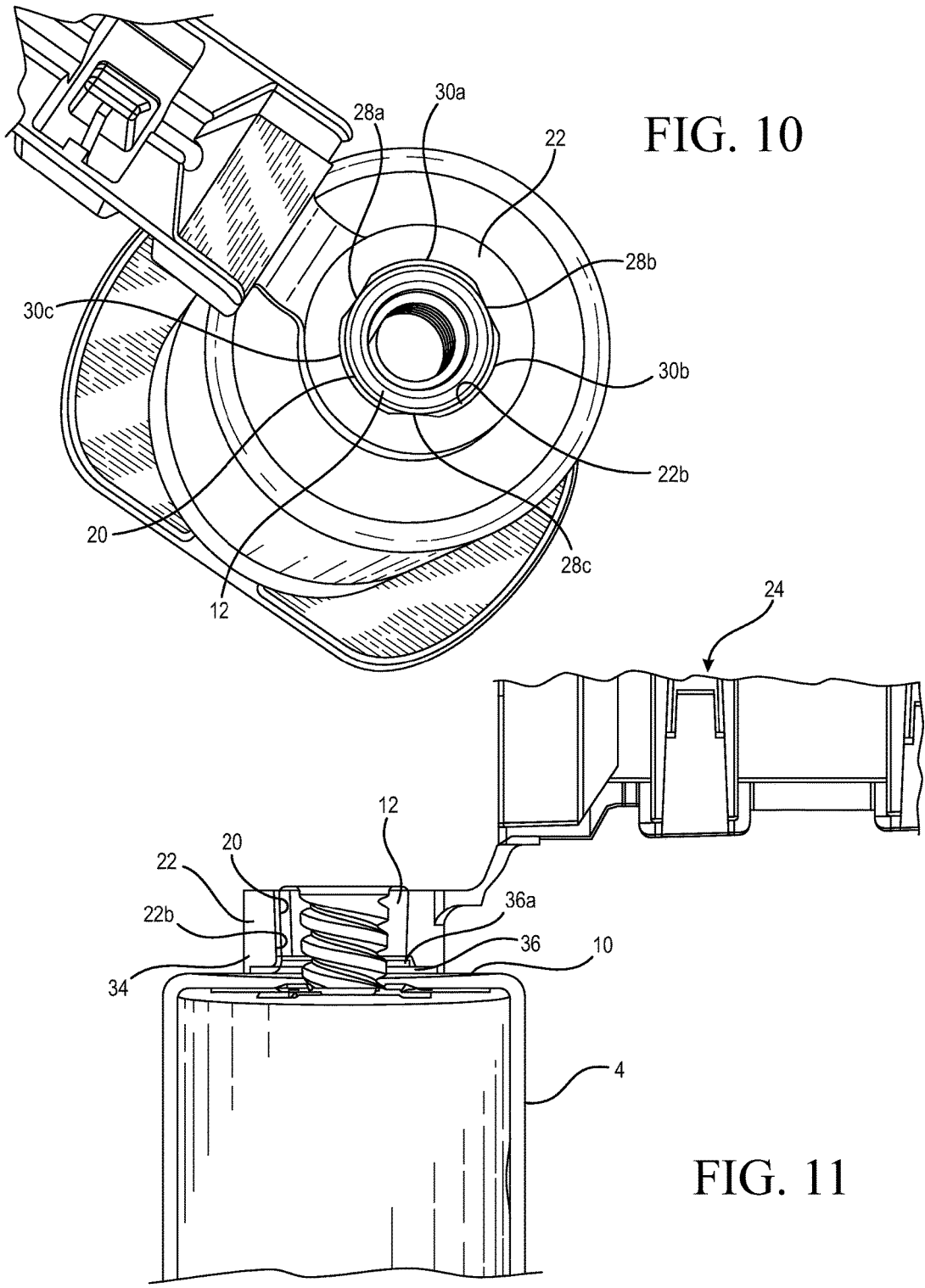

REVERSE TAPER MOUNTING OF SEPARATE COMPONENTS AND COUPLING OF DEVICES WITH REVERSE TAPER FITTINGS

FIELD OF THE INVENTION

The instant invention relates to the mounting of two plastic components together in such a way that there is controlled rotation between the components. The present invention more specifically relates to the mounting of a collar, to which a needle protection housing is hingedly attached, to the neck of a vacuum tube holder, so that controlled rotation of the collar relative to the neck of the tube holder is effected. The instant invention moreover relates to the way in which the collar and the neck are matingly coupled that provides the controlled rotation between the collar and the tube holder.

BACKGROUND OF THE INVENTION

A product under the trade name NEEDLE-PRO® has been sold by the assignee of the instant invention for a number of years. The NEEDLE-PRO® product is described in U.S. Pat. No. 5,154,285, among other patents assigned to the instant assignee. Briefly, NEEDLE-PRO® is a safety needle device that has a vacuum tube holder having a needle protection housing pivotable relative to the tube holder. In particular, the needle protection housing is hingedly attached to a collar or base, which is mounted about a neck or a receptacle end of the vacuum tube holder. As described in the '285 patent, the being sold NEEDLE-PRO® product has a circumferential protuberance, or boss, formed at the receptacle end, or neck, of the holder. A counterpart circumferential groove is formed about the inner wall of the base, so that when the base is fitted onto the receptacle end of the holder, the boss is mated to the groove so that the base is rotatable about the receptacle end. The neck, or receptacle end, of the holder has a channel or aperture that is internally threaded so that a conventional double-ended needle assembly is able to be threadedly mated thereto by means of its externally threaded needle hub. The disclosures of U.S. Pat. No. 5,154,285 and U.S. Pat. No. 5,277,311, a CIP of the '285 patent, are incorporated by reference to the disclosure of the instant application.

With the protuberance/groove configuration, the needle housing is able to be rotated about the receptacle end of the holder. So that the housing may be stopped at the desired orientation relative to the holder, the respective dimensions of the internal groove of the base and the circumferential boss at the neck are such that a given friction is provided, so that theoretically the rotation of the housing relative to the receptacle end of the holder may be controlled.

During the many years of use of the NEEDLE-PRO® product, there have been instances where the housing freely rotates about the receptacle end of the housing, and also where the friction between the base and the receptacle end is such that the base seizes to the neck when the housing is turned relative to the holder. These problems most likely result from the dimensional variances of the molded plastic base and receptacle end of the holder. In other words, if both the base and the receptacle end to which the base is to be mounted were manufactured to have the desired allowable dimensional tolerances, the assembled product would most likely have a base that may rotate in an acceptable fashion about the receptacle end. But if either or both of the base and the receptacle end to which the base is to be fitted was/were molded with their dimensions outside their respective allowable tolerances, then the base and the receptacle end may either lock up, when the housing is rotated relative to the holder, or rotate loosely.

SUMMARY OF THE PRESENT INVENTION

To eliminate the above potential problems of the NEEDLE-PRO® product, the present invention provides an improved self-adjusting mounting of the base of the housing to the neck of the holder so that a constant drag is provided between the base and the receptacle end when the housing is rotated relative to the holder, to thereby provide controlled rotation of the housing relative to the holder. At the same time, lock-up or seizure between the base of the housing and the receptacle end of the holder, when the base is rotated relative to the holder, is prevented.

To effect the controlled rotation, the present invention has the outer circumferential wall of the neck or receptacle end of the holder tapered at a given angle and the inner wall of the base or collar tapered at a reverse angle to that of the outer wall of the neck so that, when the base is press-fitted onto the neck, it is held thereat. To prevent lockup between the base and the neck, flat surfaces or equivalents such as extended ribs and protuberances are interspersely provided about the inner wall of the base. Moreover, the lower edge of the base is formed into a relatively thin walled ring, with sufficient flexibility to provide self-adjustment of the base relative to the neck by continually biasing the base to the neck even when there is flexure at or bending of the neck, relative to the body of the holder, when the base is rotated relative to the neck.

The instant invention is therefore a reverse taper design whereby the outer wall of the neck and the inner wall of the base have reverse tapers that substantially form fit to each other. To prevent lockup, flat surfaces extend longitudinally along and interspersed about the inner wall of the base break the tension between those two opposing walls that otherwise causes lockup were the inner wall of the base and the outer wall of the neck to be in intimate contact with each other. To enable the base and the neck to self-adjust when a torsional force is applied to rotate the base relative to the neck, a thin lower ring is provided at the lower edge of the base. In addition, an internal counter bore recess extends from the ring to the inner wall. When the neck flexes due to the rotation of the base thereagainst, appropriate portion(s) of the ring would bend or collapse against the cap portion of the holder due to its flexibility while the recess provides the space for the ring to bend or collapse, so that the base may continually be biased against the neck without being pushed upwards away from the neck. When the torsional force is removed, due to its elastic memory, the ring would return to its original shape while at the same time maintaining continual biasing of the base against the neck. Note that the flexure of the neck relative to the holder is relatively slight so as not to be observable by the casual observer.

The instant invention is moreover directed to an apparatus that comprises a holder that has a body including a cap having a neck projecting therefrom, the neck extending from the cap at a proximal end that is integral with the cap to a distal end, the neck having an outer circumferential wall defined by an outer diameter that increases in size from the proximal end to the distal end of the neck to form a tapered outer circumferential wall. The apparatus further comprises a base to which a needle housing is hingedly attached that has an aperture defined by a non-ending inner wall that extends between a proximal end and a distal end of the base, the inner wall having a diameter that increases in size from the proximal end to the distal end of the base to form a counterpart reverse tapered inner wall that enables the base to substantially form fit about the tapered outer circumferential wall of the neck. The respective dimensions of the tapered outer circumferential wall of the neck and the counterpart reverse tapered inner wall of the base are configured such that after the base is press-fitted onto the neck, the base is prevented form disengaging from the neck and a predetermined friction is established between the base and the neck to prevent the neck and the base from freely rotating relative to each other, and whereby the base and the neck are rotatable relative to each other when a force sufficient to overcome the predetermined friction is applied to rotate the housing with the holder relative to each other.

The present invention is also directed to a combination of a holder having a body and a neck extending from a cap portion of the holder and a base having an aperture defined by a non-ending inner wall. The neck of the holder has an outer circumferential wall defined by an outer diameter that increases in size from the proximal end of the neck to the distal end of the neck. A channel extends through the neck so that a passage into the holder is provided from the opening at the distal end of the neck through the channel into the holder. The outer circumferential wall of the neck tapers from the distal end to the proximal end at a given angle. The inner wall of the base has a diameter that tapers at an angle from the proximal end of the base to the distal end of the base that is in reverse to the given angle of the outer circumferential wall of the neck so that, when the base is press-fitted onto the neck with the proximal end of the base positioned about the proximal end of the neck, the tapered inner wall of the base substantially form fits about the tapered outer circumferential wall of the neck to prevent the base from separating from the neck and to establish a predetermined friction between the base and the neck to thereby prevent the neck and the base from rotating relative to each other absent a force sufficiently large to overcome the predetermined friction.

The present invention is further directed to a method of manufacturing a device that comprises the step of forming a holder to have a body having a cap portion, and a neck extending from the cap portion of the holder. The neck is formed to have an outer circumferential wall defined by an outer diameter that increases in size at the proximal end of the neck at the cap portion of the holder to a distal end of the neck so that the outer circumferential wall of the neck tapers from the distal end to the proximal end at a given angle. The neck has an opening at its distal end that extends into the holder. The method further comprises the step of forming a base that has a housing hingedly attached thereto. The base has an aperture defined by a non-ending inner wall that extends between a proximal end and a distal end of the base. The diameter of the inner wall of the proximal end of the base to the distal end of the base tapers at an angle that is the reverse of the given angle of the neck, so that when the base is press-fitted onto the neck with the proximal end of the base positioned about the proximal end of the neck, the tapered inner wall of the base substantially form fits about the tapered outer circumferential wall of the neck to prevent the base and the neck from disengaging from each other and to establish a predetermined friction between the base and neck to prevent the neck and the base from rotating relative to each other absent a force sufficiently large to overcome the predetermined friction.

The present invention also is directed to an apparatus, and method of manufacturing thereof, that has a first device having a neck that includes an outer circumferential wall having a first taper that extends from the base of the neck to the distal end of the neck at a first angle. The apparatus also has a second device having a collar that has an inner circumferential wall having a second taper that extends from the distal end of the collar to the base of the collar at a second angle in reverse to the first angle. The collar and the neck are mated to each other with the base of the collar passing the distal end of the neck to be in a resting position relative to the base of the neck so that the outer circumferential wall of the neck is in engagement with the inner circumferential wall of the collar. The engagement of the outer circumferential wall of the neck and the inner circumferential wall of the collar effects a friction to prevent relative rotation between the collar and the neck except when a torque that is greater than the friction is applied to rotate the collar relative to the neck.

The present invention is moreover directed to an apparatus that comprises a first device having a first connection fitting of a first configuration with an outer wall having a first taper at a first angle that extends from the base to the distal end of the first connection fitting, and a second device having a second connection fitting of a second configuration complementary to the first configuration with an inner wall having a second taper at a second angle in reverse to the first angle that extends from the distal end to the base of the second connection fitting. When the first connection fitting and the second connection fitting are mated to each other, the outer wall of the first fitting is in angled engagement with the inner wall of the second connection fitting to effect a secure connection between the first and second connection fittings.

The present invention is furthermore directed to a method of coupling two devices, comprising the steps of: forming a first device having a first connection fitting with a first configuration including an outer wall having a first taper at a first angle that extends from the base to the distal end of the first connection fitting; forming a second device having a second connection fitting with a second configuration complementary to the first configuration including an inner wall having a second taper at a second angle in reverse to the first angle that extends from the distal end to the base of the second connection fitting; and mating the first and second connection fittings to each other so that the outer wall of the first fitting is in engagement with the inner wall of the second fitting to effect a secure connection between the first and second connection fittings.

BRIEF DESCRIPTION OF THE DRAWINGS

The present invention will be best understood with reference to the following description taken in conjunction with the accompanying drawings wherein:

FIG. 10 is an enlarged perspective top view showing the relationship between the inner wall of the base and the outer wall of the neck of the holder;

FIG. 11 is a cross-sectional side view showing the base press fitted onto the neck of the holder;

DETAILED DESCRIPTION OF THE INVENTION

Figure 1:
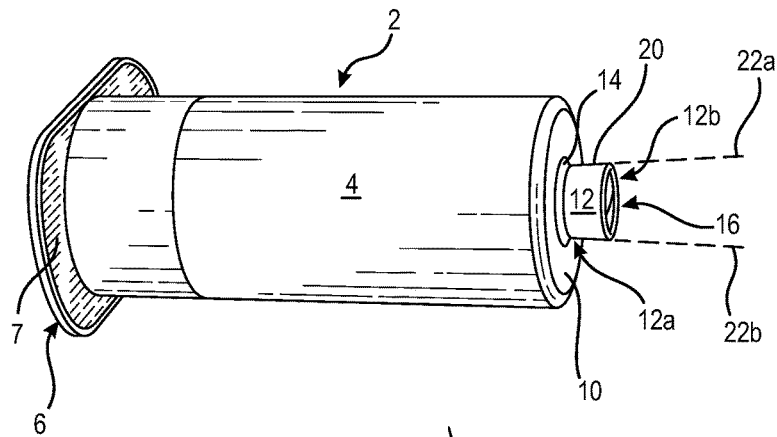
FIG. 1 is a perspective view of the vacuum tube holder of the instant invention.
Figure 9:
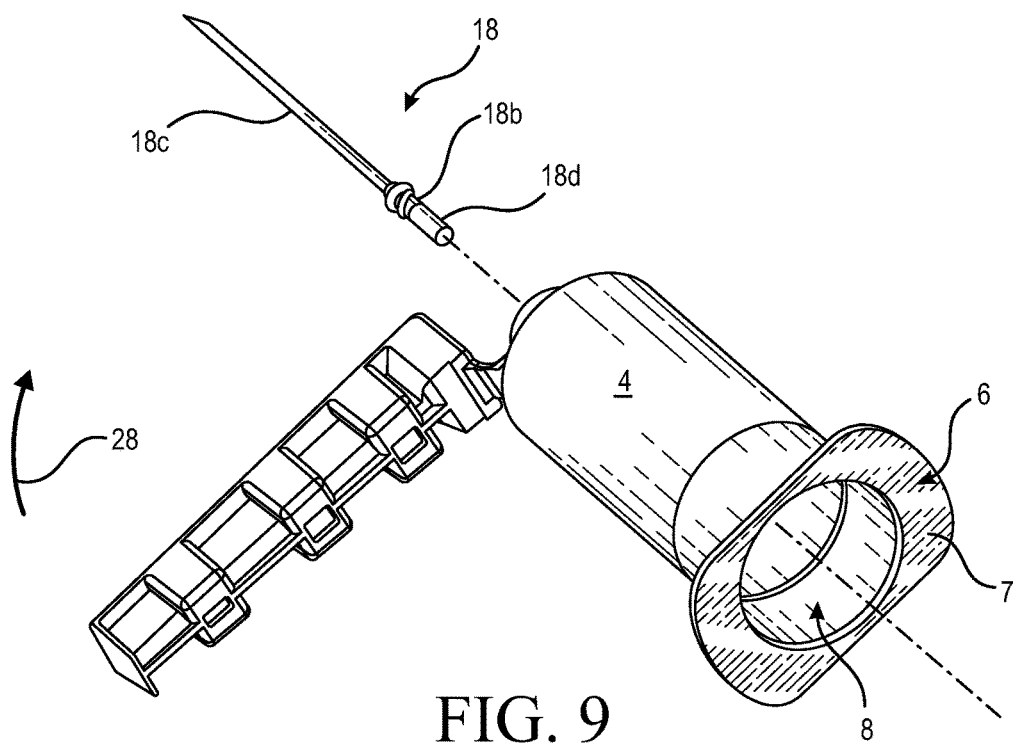
FIG. 9 is a reverse perspective view of the inventive safety needle device and the needle assembly to be mated thereto.

With reference to FIG. 1, a vacuum tube holder 2 is shown to have a main body 4 that has a proximal end 6 whereat a rest or foot plate 7 is provided. As shown in FIG. 9, an opening 8 is provided at the proximal end of holder 2 whereinto a conventional vacuum tube, not shown, may be inserted as is well known in the art. Body 4 has at its distal end a cap, or cap portion, 10 whereat a receptacle end, or neck, 12 of holder 2 extends. As shown, neck 12 has a proximal end 12a that is an integral continuation of cap 10, by way of a chamfer 14, to a distal end 12b. As is conventionally known, neck 12 has a through bore or channel 16 that extends from its distal end 12b into the interior of body 4 of holder 2. As is further well known, channel 16 is threaded so as to be able to threadingly mate with a needle assembly, such as 18 shown in FIG. 9, by way of the latter's needle hub 18b. Needle assembly 18 may be a conventional double-ended needle assembly having an outwardly extending end needle 18c used to prick a patient, and another end needle inserted into the interior of holder body 4 used to pierce the rubber septum that seals the front end of the vacuum tube inserted into body 4 of tube 2 via its opening 8. As shown in FIG. 9, the end needle to be inserted into the interior of body 4 is enclosed by an elastomeric boot 18d.

Figure 2:
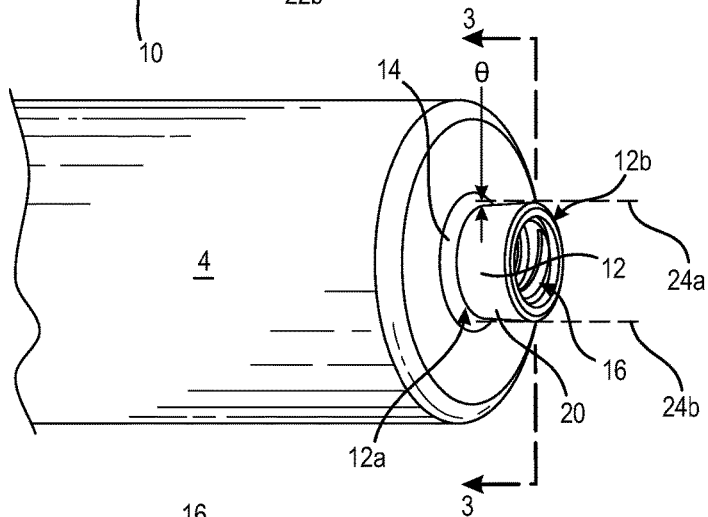
FIG. 2 is an enlarged view of the receptacle end, or neck, of the holder of FIG. 1.

Neck 12 has an outer circumferential wall 20 that extends from proximal end 12a to distal end 12b at an increasing incline amplified by the two dotted lines 20a and 22b in FIG. 1. Thus, the outer wall of neck 12 has a taper due to the size or dimension of the diameter of the neck increasing from proximal end 12a to distal end 12b at a given angle (or the angle shown in FIG. 2 with reference to the plane whereat the distal end 12b of neck 12 lies along). Putting it differently, neck 12 slopes downward at an incline from its distal end 12b towards its proximal end 12a. From empirical studies, it was found that the angle, designated by θ, may be from approximately 2 degrees to 10 degrees, with an optimal incline being from approximately 3 degrees to 6 degrees, with reference to an imaginary circular plane represented by the dotted parallel lines 24a and 24b.

Figure 3:
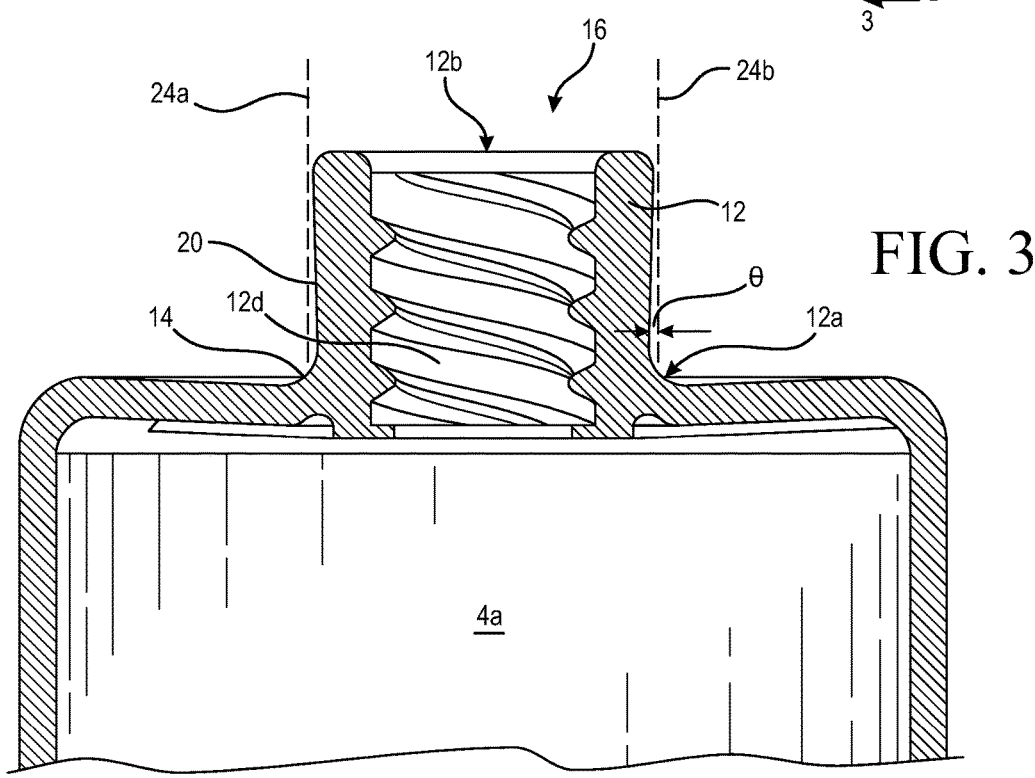
FIG. 3 is a cut-away cross-sectional view, along cut line 3-3, of the neck and upper portion of the holder of FIG. 2.

The taper of the outer wall 20 of neck 12 is further shown in the cross-section view of FIG. 3, being represented by an angle θ with reference to the pair of parallel lines 24a and 24b. Also shown in FIG. 3 is the internal screw thread 12d of neck 12 which, as discussed above, is used to threadingly mate with a needle hub of a double-ended needle assembly, so that one end of the needle extends away from neck 12 while the other end of the needle extends into the interior 4a of body 4.

Figure 4:
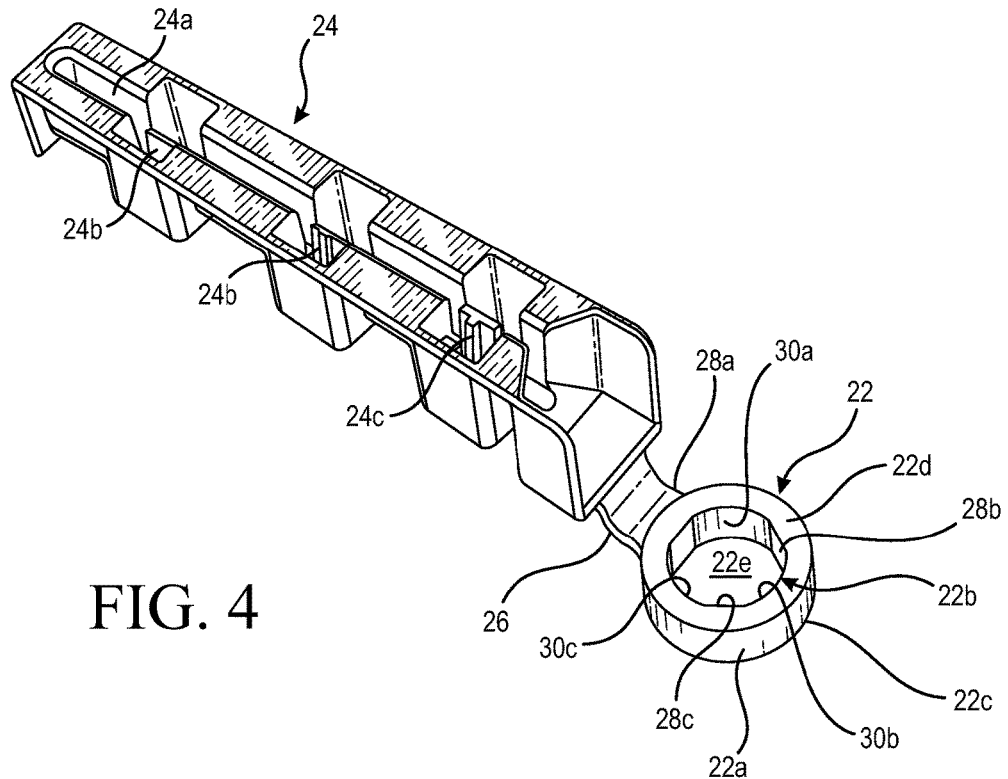
FIG. 4 is a perspective view of the base, or collar, of the instant invention with a needle protection housing hingedly attached thereto.

FIGS. 4-7 are illustrations of the collar, or base 22 to which a needle protection housing 24 is hingedly connected by way of a living hinge 26. FIG. 4 is a top perspective view of base 22 and housing 24. As shown, base 22 is in the shape of a collar or ring having an outer circumferential wall 22a and a non-ending inner wall 22b. Needle protection housing 24 is shown to have a longitudinal slot 24a along substantially its entire length whereby a needle such as needle 18c (FIG. 9) passes when housing 24 is pivoted in the direction as indicated by directional arrow 28 (FIG. 9) to cover the needle, assuming that the needle assembly 18 has been matingly attached to neck 12 of holder 4. Inside housing 24 a plurality of lock mechanisms in the form of hooks 24b would grasp the needle to fixedly retain housing 24 to the needle in the manner as disclosed in the aforenoted incorporated by reference '285 patent. Base 22, with reference to FIGS. 4 and 7, has a proximal end 22c and a distal end 22d.

Figure 5:
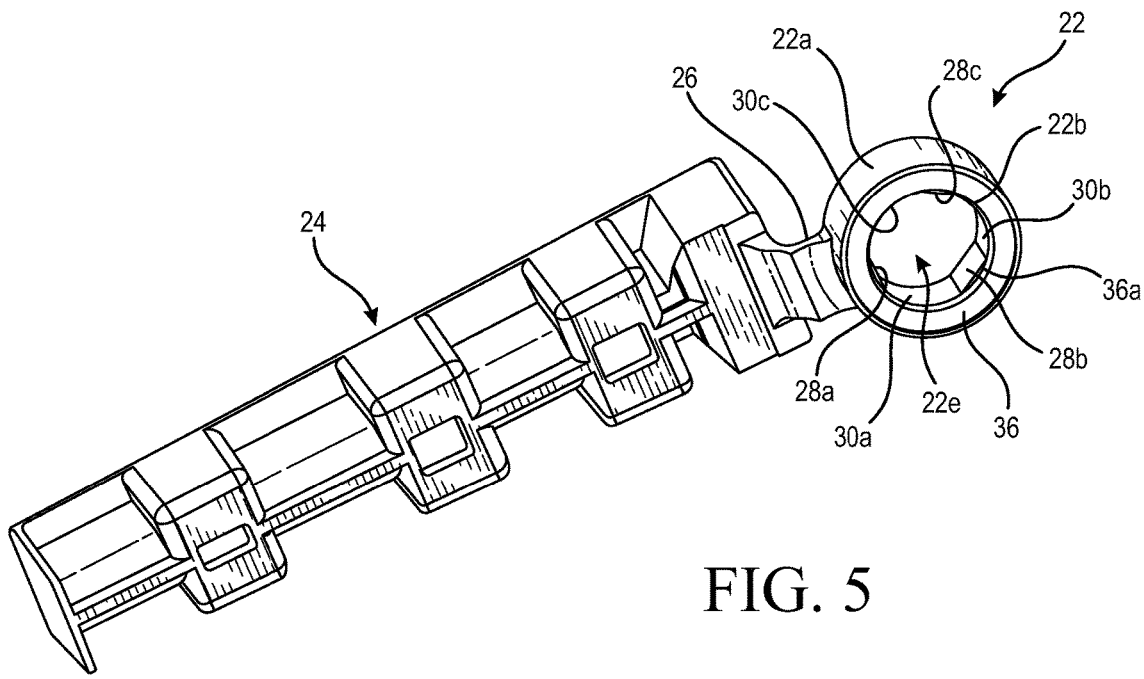
FIG. 5 is a perspective bottom view of the base of FIG. 4.
Figure 6:
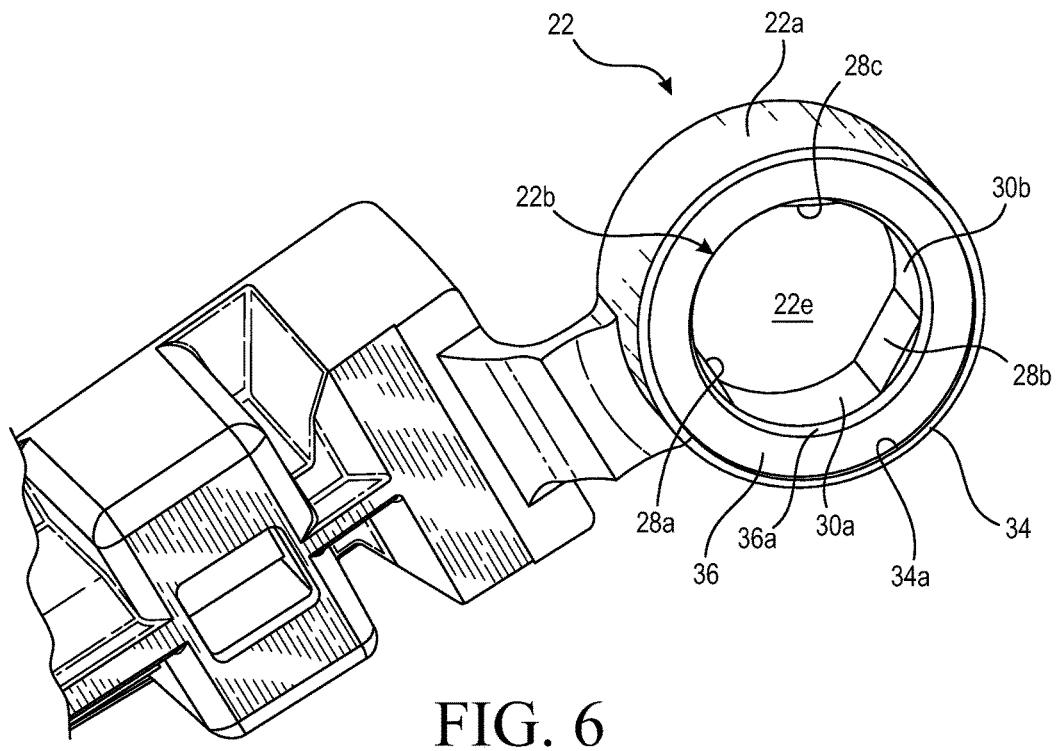
FIG. 6 is an enlarged bottom view of the base of the FIG. 5 holder.

Base 22 has an aperture or opening 22e that is defined by the non-ending inner wall 22b, which may be considered an inner circumferential wall that is divided into a number of sections with non-circumferential sections alternating with circumferential sections. As shown in FIGS. 4-6, a number of flat surfaces or flats 28a, 28b and 28c that extend longitudinally between proximal end 22c and distal end of 22d of base 22 are interspersed about the inner wall 22b. Alternating with and separating flats 28a-28c are circumferential surfaces 30a, 30b and 30c. Flats 28a, 28b and 28c would be in contact with the outer wall of the neck, when base 22 is press-fitted onto the neck. Flats 28a-28c ensure that the inner wall 22b of base 22 does not lock up, or seized with the outer wall 20 of neck 12, when base 22 is rotated relative to neck 12 by preventing continuous or non-ending intimate contact between the inner wall 22b and the outer wall 20, as will be discussed further infra.

Figure 7:
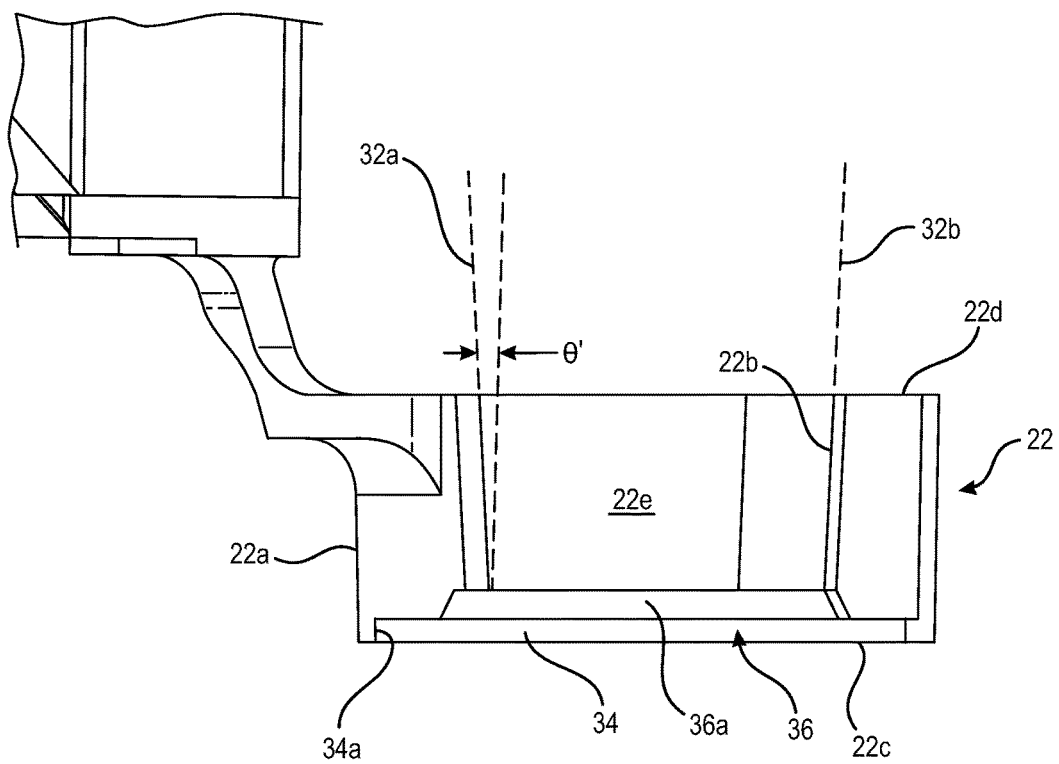
FIG. 7 is a cross-sectional view of the base of the instant invention.
Figure 8:
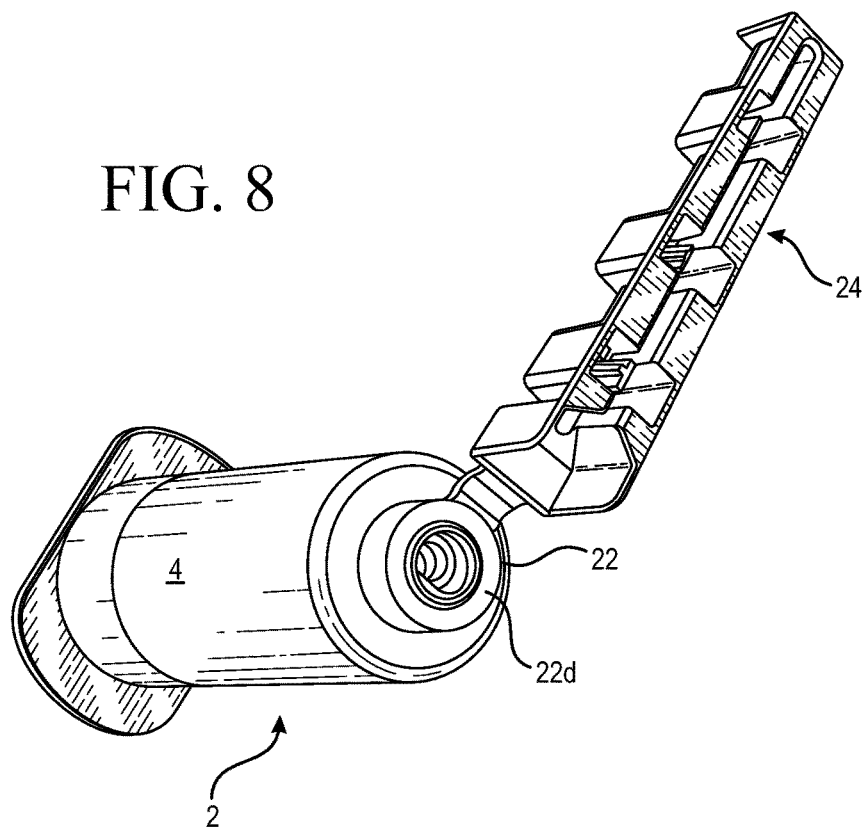
FIG. 8 is a perspective view of the assembled safety needle device of the instant invention with the base having been fitted onto the neck of the holder.

As best shown in the cross-sectional view of base 22 in FIG. 7, the non-ending inner wall, or simply the inner circumferential wall 22b, of base 22 has a diameter that increases in size from its proximal end 22c to its distal end 22d. This increase in the dimension or size of the diameter of inner wall 22b, or opening 22e, of the base is amplified by the double dotted lines 32a and 32b to have an angle θ' that is the reverse of the angle θ of the taper of outer wall 20 of neck 12. In other words, the inner wall 22b, or the opening 22e, of base 22 has a reverse taper to that of the outer wall of neck 12. The respective tapers of outer wall 20 of neck 12 and the inner wall 22b of base 22 are configured such that opening 22e defined by the inner wall 22b substantially form fits about neck 12, more specifically the outer wall 20 of neck 12, per shown in FIGS. 8, 10 and 11.

With further reference to the enlarged view of base 22 per shown in FIG. 6 and the cross-sectional view shown in FIG. 7, a ring 34 having a relatively thin wall is formed as part of the outer wall 22a of base 22 at its proximal end 22c. Ring 34 has a height 34a so that an annular recess 36 is formed internal to ring 34 at proximal end 22c. Recess 36 extends into a counterbore space, or simply counterbore 36a that may be considered to be a continuation of recess 36. Counterbore 36a is configured as a counterpart to chamfer 14, which may also be considered as a radius, of holder 2 (FIG. 1) that integrates cap 10 with the proximal end 12a of neck 12. Recess 36, in combination with counterbore 36a, ensure that base 22 substantially form fits about neck 12 with yet sufficient space separating inner wall 22b of base 22 from the chamfered and cap portions 14, 10 of holder 2. With support contact from cap 10 of holder 2, ring 34 biases base 22 upwardly against neck 12, so that base 22 is self-adjustedly fitted to neck 12 even when neck 12 flexes, as will be discussed in further detail below.

With references to FIGS. 8-11, base 22 is shown to have been press-fitted onto neck 12 of holder 2, with the top surface of the base, referenced by distal end 22d, being slightly below the top, or the distal end 12b of neck 12. By having the distal end of the neck slightly above the distal end of the base prevents potential interference to the mating of the needle assembly 18 into the threaded channel 16 of neck 12.

With reference to the enlarged view of base 22 fitted to neck 12 in FIG. 10, note that the outer wall 20 of neck 12 is in intimate contact only with flats 28a, 28b and 28c at the inner wall of base 22. Thus, pockets of spaces are formed between circumferential surfaces 30a, 30b and 30c of the inner wall of base 22 and the outer wall 20 of neck 12. This intermittent contact between the inner wall of base 22 and the outer wall of neck 12 breaks up any potential tension due to intimate contact between the respective tapered walls of the neck and base to thereby ensure that there is no lock up or seizure between inner wall 22b of base 22 and the outer wall 20 of neck 12, when base 22 and neck 12 are rotated relative to each other.

Although flat surfaces 28a-28c are shown, it should be appreciated that the inner circumferential wall of base 22 may instead be provided with other types of non-circumferential contact surfaces such as longitudinal ribs or protrusions interspersed thereabout so that only those non-circumferential surfaces would come into contact with the outer wall of the neck. Conversely, it is envisioned that the protrusions, ribs, flats and other equivalent means may be provided at the outer wall of the neck while the inner circumferential wall of the base is smooth to prevent the base and the neck from locking up, when the housing is moved to rotate the base relative to the neck.

When a rotational force is applied to move the base relative to the neck, due to the elasticity nature of the base and the holder since both components are made from plastics material such as polypropylene (PP), the neck of the holder tends to flex relative to the body of the holder. This flexure movement of the neck may cause a portion of the also being tilted base (since the base is mounted about the neck) to come into contact with the cap portion of the holder. As a result, if the circumferential wall of the base were to have the same thickness throughout, due to the abutment of the tilted bottom of the base with the cap of the holder, the base is forced upwards away from the neck, despite the reverse tapers of the neck and the base. To overcome this potential problem, as discussed above, ring 34 is formed at the lowermost portion of base 22 to have a wall that is substantially thinner than the rest of the base so that it is more flexible than the rest of the base. Given its flexibility, when there is flexure or tilting of the neck relative to the body of the holder due to rotational force applied thereagainst, the portion of ring 34 that is tilted downward would flex or collapse onto the cap of the holder 2 to absorb the downward movement of the base, instead of biasing base 22 upwards away from neck 12. As a result, base 22 is continually and self adjustedly biased against neck 12, while at the same time not forced by the flexure of the neck to eventually pop or push off from neck 12. Ring 34 therefore acts as a mechanism to self-adjust the positioning of the base relative to the neck. As discussed above, the flexing of the neck relative to the holder body in most instances is quite slight and therefore may not be noticed by casual observation.

The contact between ring 34 of base 22 and cap 10 of holder 4 may best be seen in FIG. 11. FIG. 11 also shows recess 36 and counterbore 36a, and the space between the chamfered area of neck 12 relative to recess 34. The counterbore recess 36 at the distal end 22c of the base provides the space to allow the ring to flex without the proximal end of the base coming into contact with the chamfer 12 of neck 12. Note that even though there is a frictional force between the bottom edge of the ring and the cap of the holder, the main frictional force that causes the friction force or drag between the base and the neck, when the base is rotated relative to the neck, results from flats 28a-28c making contact with the outer wall 20 of neck 12. Thus, with the reverse tapers for the neck and the base being configured such that inner wall 22b of base 22 substantially form fits about outer wall 20 of neck 12, and with ring 34 providing the force to bias the base to the neck and also to absorb flexure movements of the neck, base 22 is mounted about neck 12 in a self-adjusting manner.

The friction between the contacting surfaces of the inner wall of the base and the outer wall of the neck may be pre-determined by empirical trials or studies so that the base may be rotated relative to the neck smoothly with a proper drag in a controlled and smooth manner, when a force sufficiently larger than the predetermined friction is applied to the housing to rotate the base relative to the neck. Due to the predetermined friction, once the force is removed, the rotation of the base relative to the neck would stop to thereby position the needle protection housing at the appropriate orientation relative to the holder, for example enabling the user to readily observe the bevel of the needle as the needle is intravenously inserted into the patient. Thus, the inventive mounting of reverse tapered walls effects a controlled rotation of the components, i.e., the base of the needle protection housing and the neck of the tube holder as discussed above.

Even though the instant invention is discussed with reference to a medical device such as the Vacutainer Holder attached with a rotatable needle protection housing, it should be appreciated that the inventive reverse taper configuration may also be applicable for other plastic components that are mounted relative to each other to achieve controlled rotation of one component relative to the other at different orientations with a controlled drag.

Figure 12:
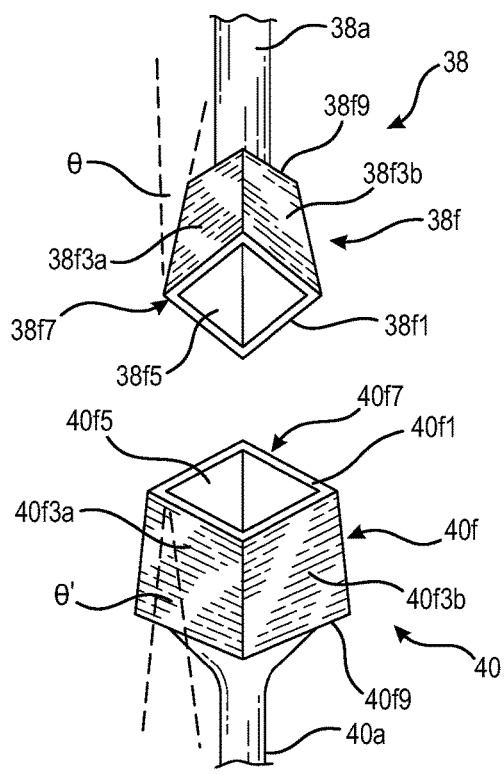
FIG. 12 is an illustration of an alternative embodiment of the instant invention showing the two connection fittings of the devices to be coupled have complementary reverse tapered square configurations.
Figure 14:
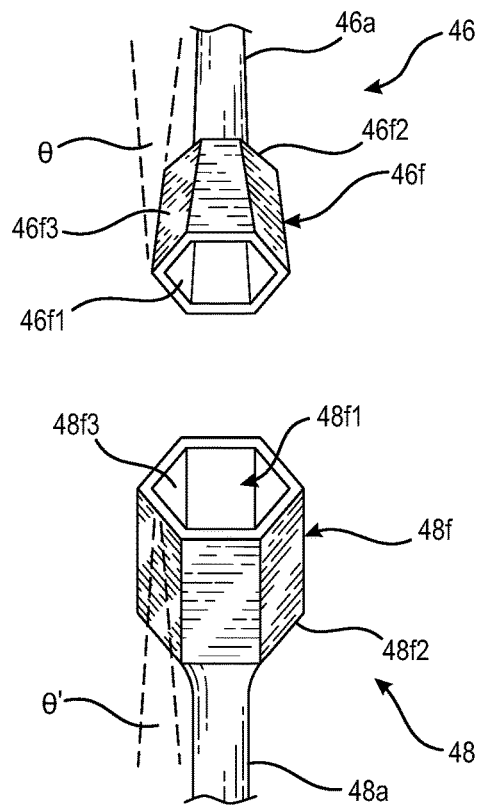
FIG. 14 is yet another exemplar illustration of complementary connection fittings of devices to be connected that have reverse tapered multi-sided configurations.
Figure 13:
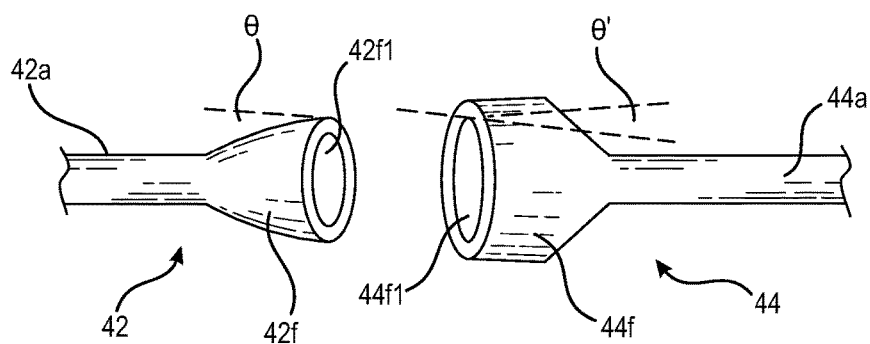
FIG. 13 illustrates another exemplar reverse tapered coupling where the two connection fittings of the devices to be connected have non-circumferential complementary reverse tapered configurations.

The inventive reverse taper configuration concept may also be incorporated to connection or end fittings to connect or couple two components, parts or devices. In addition to using circular shaped connection fittings, to couple devices that do not require controlled rotation, configurations for the connection fittings may have complementary shapes that are other than circular or round. For this embodiment, the connection fittings (or simply fittings) of the components, parts or devices (may be referred to simply as devices) have coacting surfaces that are not rounded or circumferential. Some such non-circular exemplar reverse tapered coacting surfaces may include oval, square or rectangular, hexagonal. multi-sided, etc. The devices may include conduits, tubings and catheters that may be used, but not necessarily, in medical settings to convey fluid and/or materials along the coupled devices. The devices may also include fluid or material non-conveying components if the purpose of the fittings is simply to securely couple the two components. Of course, one of the to be coupled devices may be the vacuum tube holder and the other the needle protection housing as described above, with the connection fittings being the neck and the collar pivotally connected to the housing. As with the tube holder embodiment described above, the reverse tapered connection fittings of the devices are made of conventional medical plastics (and possibly a shape memory or retaining metal) that have the elasticity to enable those fittings to be press fitted together and then return to their original shapes to effect the coupling. With non-circular reverse tapered coacting coupling connection fittings, the devices that are connected with those fittings are not, and are not meant to be rotatable. FIGS. 12, 13 and 14 hereinbelow illustrate examples of some non-circumferential reverse taper fittings.

With reference to FIG. 12, two to be coupled or connected devices 38 and 40 are shown. Devices 38 and 40 each have a conduit (or catheter or tubing) 38a and 40a, respectively, extending to corresponding complementary connection fittings 38f and 40f. Each of the connection fittings 28f and 40f is shown to have a distal square end designated 38/1 and 40/1, respectively. The connection fittings each are formed by four sidewalls, 38/3a-38/3d for fitting 38f (with only sidewalls 38/3a and 38/3b labeled), and sidewalls 40/3a-40/3d for fitting 40f (with only sidewalls 40/3a and 40/3b labeled). As the exemplar devices 38 and 40 are conduits, respective openings 38/5 are formed by the respective four sidewalls of each of the fittings 28 and 40.

For the FIG. 12 embodiment, fittings 38 and 40 are shown to have complementary configurations that enable those fittings to mate to each other. Connection fitting 38 may be considered a male fitting while connection fitting 40 may be considered the female fitting. The distal end 38/1 of fitting 38f has a dimension slightly smaller than that of distal opening 40/5 of fitting 40f. Given that the connection fittings 38f and 40f are molded or manufactured from plastics material and therefore each have the characteristic elasticity of plastics material, fitting 38f may be matingly inserted into fitting 40f, when the two connection fittings are mated to each other, for example by press fitting. Once mated to and positioned within the interior cavity of fitting 40f, the outer surfaces of the sidewalls 38/3a-38/3d of fitting 38f would return to their memory positions to be in intimate contact with the corresponding inner surfaces of sidewalls 40/3a-40/3d of fitting 40f. For the sake of brevity, the outer surfaces of the sidewalls 38/3a-38/3d of fitting 38f may simply be referred to as the outer sidewalls of fitting 38f, while the inner surfaces of sidewalls 40/3a-40/3d may simply be referred to as the inner sidewalls of fitting 40f.

As exaggeratedly shown in FIG. 12, each of the outer sidewalls of fitting 38f is tapered from the distal end 38/7 of fitting 38f to its proximal end 38/9 at an angle θ, which may be the same angle that was described above with respect to the tube holder embodiment. Connection fitting 40f is also shown to have four sidewalls where there is a reverse taper provided at each of the inner sidewalls at an angle θ' that extends from the distal opening 40/7 of fitting 40f to its proximal end 40/9. As described above with respect to the tube holding embodiment, angles θ and θ' are the reverse of each other so that the outside sidewalls of connection fitting 38f and the inside sidewalls of connection fitting 40f have reverse tapers. Accordingly, once connection fittings 38f and 40f are press fitted together, not only are the corresponding outer sidewalls of fitting 38f and the inner sidewalls of devices 38 in intimate contact with each other, that the fittings are reverse tapered to each other means that fittings 38f and 40f are securely coupled together. As a result, devices 38 and 40 are securely coupled to each other. In the exemplar embodiment shown in FIG. 12, after coupling, given that devices 38 and 40 are conduits, a fluid, or other material, is passable or can be conveyed between the two devices.

Note that although the connection fittings are shown with respective openings to allow passing of fluid or other material between the devices, it should be appreciated that in the event that the devices to be coupled are devices that are not used to transfer fluid or other material therebetween, no opening may need to be formed for the male connection fitting of those devices. In other words, openings 38/5 for fitting 38f is not needed for mating to opening 40/5 of fitting 40f, which may have a closed proximal end 40/9. It should be appreciated that those closed ended connection fittings nonetheless are reverse tapered to each other so that once press-fittedly connected or mated to each other, devices 38 and 40 are securely coupled together, and would ordinarily not be removable from each other unless a greater than normal force is applied to pull or remove the connection fittings away from each other. Such non-fluid or material transfer devices that are coupled by reverse tapered fittings may for example be rods or shafts.

FIG. 13 is an illustration of another embodiment of to be connected fittings having complementary reverse tapered configurations that allow for easy engagement of two devices. In the embodiment shown in FIG. 13, to be connected or coupled devices 42 and 44 each have connection fittings 42f and 44f, respectively, extending from corresponding tubings 42a and 44a. The connection fittings 42f and 44f each have an oval shape with respective openings 42/1 and 44/1. The outside wall of fitting 42f inclines from opening 42/1 to the junction where the tubing meets tubing 42a at an angle θ. The wall, specifically the inside wall of fitting 44f has a reverse incline from opening 44/1 to tubing 44a at an angle θ'. Thus, when connection fittings 42f and 44f are mated together by for example press-fitting, devices 42 and 44 are securely coupled together. As in the case of the connection fittings having the square configuration shown in FIG. 12, the oval shaped configuration of the connection fittings of FIG. 13 embodiment prevents devices 42 and 44 from rotating relative to each other once they are coupled by means of their respective connection fittings 42f and 44f. Also as described above, even though openings are shown in the FIG. 13 oval shape configured connection fittings to enable fluid to pass between devices 42 and 44 once those connection fittings are matingly coupled to each other, in those cases where no fluid or material is to be transferred between the devices, opening 42/1 of connection fitting 42 is not needed, i.e., fitting 42 may be a solid fitting or its distal end is sealed or closed.

FIG. 14 illustrates yet another embodiment of the instant invention in which the connection fittings for connecting two devices together have complementary reverse tapered configurations that are not circular or round. In the embodiment shown in FIG. 14, devices 46 and 48 have connection fittings 46f and 48f, respectively, that are multi-sided, in this instance in the shape of a hexagon or a hexagonal configuration. Fittings 46f and 48f extend respectively from tubings 46a and 48a, or some other conduits or shafts or members. As with the earlier embodiments, fitting 46f has a taper that extends from its distal end, represented by distal opening 46/1, to its proximal end 46/2 along each of its sidewalls 46/3 at an angle θ. Connection fitting 48f for device 48, on the other hand, is tapered from its distal end, represented by the open end of opening 48/1 to its proximal end 48/2, along its sidewalls 48/3 (assuming the sidewalls do not vary in thickness along their respective lengths). The taper for the inner sidewalls of connection fitting 48f is labeled θ' which is reverse of the angle θ for the outer sidewalls of connection fitting 46f. As a consequence, when connection fitting 46f is matingly inserted into opening 48/1 of fitting 48f, devices 46 and 48 are securely coupled together, due to the complementary reverse tapered configurations of their respective connection fitting 46f and 48f. As discussed above, opening 46/1 for fitting 46f is necessary only if devices 46 and 48 are tubings or conduits or catheters, that are connected to enable fluid or other material to pass between those devices. But if no fluid or other material is to be conveyed between the devices, then fitting 46f does not have to have an opening, and in fact may be a solid connection fitting with the same tapered outer sidewall configuration.

For the coupling of the devices with connection fittings that have complementary reverse tapered configurations, even though only three different embodiments are shown, it should be appreciated that other configurations for the connection fittings of to be coupled devices may also be used, so long as the outer sidewall(s) of one device and the inner sidewall(s) of the other device are reverse tapered and the connection fittings have complementary configurations that allow the fittings to be matingly connected to each other to thereby couple the devices together. it should further be appreciated that even though the exemplar embodiments of FIGS. 12-14 each show that the outer wall of the female fittings 40f, 44f and 48f have the same configured shapes as their respective inner walls, in practice, the outer walls of the female fittings may have shapes different form their respective openings (or bores) so long as the openings of those female fittings maintain the same complementary configurations as their respective male fittings that are to be mated to those openings. In other words, the sidewall(s) of the female fittings may have different thickness along different portions thereof. For example, the female fitting 48f of the FIG. 14 embodiment may have a circumferential outer wall while its inner wall would continue to have six sidewalls forming a hexagonal configuration that is complementary to the hexagonal configuration of the male fitting 46f. Thus, the male and female fittings 46f and 48f for the example continue to have configurations that are complementary to each other since the portions of those fittings that are to be fittingly connected to or matable with each other are in complement with each other.

It should be appreciated that the present invention is subject to many variations, modifications, and changes in detail. Thus, all matter described throughout this specification and shown in the accompanying drawings should be interpreted as illustrative only and not in a limiting sense. Accordingly, it is intended that this invention be limited only by the spirit and scope of the hereto appended claims.

The invention claimed is:

1. Apparatus, comprising:
a holder having a body including a cap having a neck projecting therefrom, the neck extending away from the cap from a proximal end that is integral with the cap to a distal end, the neck having an outer circumferential wall defined by an outer diameter, the outer diameter increasing in size from the proximal end of the neck to the distal end of the neck to form a tapered outer circumferential wall;
a base to which a needle housing is hingedly attached having an aperture defined by a non-ending inner wall that extends between a proximal end and a distal end of the base, the inner wall having a diameter that increases in size from the proximal end of the base to the distal end of the base to form a counterpart reverse tapered inner wall that enables the base to substantially form fit about the tapered outer circumferential wall of the neck;
wherein the respective dimensions of the tapered outer circumferential wall of the neck and the counterpart reverse tapered inner wall of the base are configured such that, after the base is fitted onto the neck, the base is prevented from disengaging from the neck and a predetermined friction is established between the base and the neck to prevent the neck and the base from freely rotating relative to each other; and
whereby the base and neck are rotatable relative to each other when a force sufficient to overcome the predetermined friction is applied to rotate the housing and the holder relative to each other.

2. Apparatus of claim 1, wherein the inner wall of the base comprises a plurality of flat surfaces extending between the proximal and distal ends of and interspersed about the inner wall to be in contact with the outer wall of the neck.

3. Apparatus of claim 1, wherein the inner wall of the base comprises a plurality of longitudinal protrusions extending between the proximal and distal ends of and interspersed about the inner wall to be in contact with the outer wall of the neck.

4. Apparatus of claim 1, wherein the tapered outer wall of the neck comprises a taper having an angle of approximately from 2 degrees to 10 degrees from the distal end to the proximal end of the neck; and
wherein the tapered inner wall of the base comprises a taper having an angle in reverse to the angle of the neck.

5. Apparatus of claim 1, wherein the proximal end of the base comprises a circumferential recess defined between a ring formed from the lower rim of the outer wall and the inner wall that defines the aperture of the base, the ring making contact with the cap of the holder.

6. Apparatus of claim 1, wherein the neck has a channel that extends into the holder, the channel being threaded to receive a needle assembly.

7. Apparatus of claim 1, wherein the housing comprises at least one lock mechanism for non-removably grasping a needle attached to the holder when the housing is pivoted to a position in alignment with the longitudinal axis of the holder.

8. Apparatus of claim 1, wherein the holder comprises a tube holder having an open end whereinto a vacuum tube may be inserted so that its sealed end may be pierced by one end of a double-ended needle of a needle assembly mated to the neck to establish a fluid path between the inside of the vacuum tube and an other end of the double ended needle.

9. In combination,
a holder having a body and a neck extending from a cap portion of the holder, the neck having an outer circumferential wall defined by an outer diameter, the outer diameter increasing in size from the proximal end of the neck at the cap portion of the holder to a distal end of the neck that has an opening of a channel into the holder so that the outer circumferential wall of the neck tapers from the distal end to the proximal end at a given angle;
a base having an aperture defined by a non-ending inner wall that extends between a proximal end and a distal end of the base, the diameter of the inner wall from the proximal end of the base to the distal end of the base tapers at an angle in reverse to the given angle of the outer circumferential wall of the neck so that, when the base is fitted onto the neck with the proximal end of the base positioned about the proximal end of the neck, the tapered inner wall of the base substantially form fits about the tapered outer circumferential wall of the neck to prevent the base from separating from the neck.

10. Combination of claim 9, wherein the inner wall of the base comprises a plurality of flat surfaces alternating with a plurality of circumferential surfaces.

11. Combination of claim 9, wherein a predetermined friction is established between the base and the neck when the base form fits about the neck to thereby prevent the neck and the base from rotating relative to each other absent a force sufficiently large to overcome the predetermined friction.

12. Combination of claim 11, further comprising:
contact surface means interspersedly provided about the inner wall of the base or the outer wall of the neck to effect the predetermined friction between the neck and the base to enable controlled rotation between the base and the holder, and to prevent lockup between the neck and the base.

13. Combination of claim 9, wherein the proximal end of the base comprises a ring formed from the lower portion of the outer wall, a recess extending from the ring to the aperture of the base, the ring providing flexibility to ensure the base stays in place relative to the neck and to continually bias the base to the neck.

14. Combination of claim 9, wherein the tapered outer wall of the neck comprises a taper of approximately from 2 degrees to 10 degrees from the distal end to the proximal end of the neck.

15. Combination of claim 14, wherein the tapered outer wall of the neck comprises a taper of approximately from 3 degrees to 6 degrees from the distal end to the proximal end of the neck.

16. Combination of claim 9, further comprising a needle housing hingedly attached to the base, and a needle assembly having a hub matingly attached to the channel of the holder.

17. A method of manufacturing a device, comprising the steps of:
(a) forming a holder to have
a body having a cap portion,
a neck extending from the cap portion of the holder, the neck having an outer circumferential wall defined by an outer diameter, the outer diameter increasing in size from the proximal end of the neck at the cap portion of the holder to a distal end of the neck so that the outer circumferential wall of the neck tapers from the distal end to the proximal end at a given angle,
an opening at the distal end of the neck of extending into the holder;
(b) forming a base to have
a housing hingedly attached thereto,
an aperture defined by a non-ending inner wall that extends between a proximal end and a distal end of the base, the diameter of the inner wall from the proximal end of the base to the distal end of the base tapers at an angle in reverse to the given angle;
wherein when the base is fitted onto the neck with the proximal end of the base positioned about the proximal end of the neck, the tapered inner wall of the base substantially form fits about the tapered outer circumferential wall of the neck to prevent the base and the neck from disengaging from each other, and to establish a predetermined friction between the base and the neck to prevent the neck and the base from rotating relative to each other absent a force sufficiently large to overcome the predetermined friction.

18. Method of claim 17, wherein step a further comprises the steps of:
extending a plurality of flat surfaces between the proximal and distal ends of the inner wall of the base; and
alternating the flat surfaces with circumferential surfaces about the inner wall.

19. Method of claim 17, wherein the step (b) further comprises the step of:
forming a ring from the lower portion of the outer wall and a recess between the ring and the aperture of the base to self adjustedly bias the base to the neck.

20. Method of claim 17, wherein the step (a) further comprises the step of:
tapering the outer wall of the neck to an angle of approximately from 2 degrees to 10 degrees from the distal end to the proximal end of the neck; and
wherein step (b) comprises the step of:
tapering the inner wall of the base to have an angle in reverse to the angle of the outer wall of the neck.

21. Method of claim 17, further comprising the steps of:
matingly attaching a needle assembly to the neck of the holder; and
providing at least one lock mechanism in the housing for grasping a needle of the needle assembly when the housing is pivoted to a position in alignment with the longitudinal axis of the holder.

* * * * *